US011129620B2

(12) United States Patent
Sgroi

(10) Patent No.: US 11,129,620 B2
(45) Date of Patent: Sep. 28, 2021

(54) ADAPTER ASSEMBLY INCLUDING A REMOVABLE TROCAR ASSEMBLY

(71) Applicant: Covidien LP, Mansfield, MA (US)

(72) Inventor: Anthony Sgroi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 29 days.

(21) Appl. No.: 16/735,835

(22) Filed: Jan. 7, 2020

(65) Prior Publication Data
US 2020/0138442 A1 May 7, 2020

Related U.S. Application Data

(63) Continuation of application No. 14/994,457, filed on Jan. 13, 2016, now Pat. No. 10,524,797.

(51) Int. Cl.
*A61B 17/115* (2006.01)
*A61B 17/34* (2006.01)
*A61B 17/00* (2006.01)
*A61B 90/00* (2016.01)

(52) U.S. Cl.
CPC .......... *A61B 17/1155* (2013.01); *A61B 17/34* (2013.01); *A61B 2017/0046* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2090/0813* (2016.02)

(58) Field of Classification Search
CPC ............................ A61B 17/1155; A61B 17/34
USPC ........................................................ 227/175
See application file for complete search history.

(56) References Cited

U.S. PATENT DOCUMENTS

| | | | |
|---|---|---|---|
| 2,777,340 A | 1/1957 | Hettwer et al. |
| 2,957,353 A | 10/1960 | Babacz |
| 3,111,328 A | 11/1963 | Di Rito et al. |
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,695,058 A | 10/1972 | Keith, Jr. |
| 3,734,515 A | 5/1973 | Dudek |

(Continued)

FOREIGN PATENT DOCUMENTS

| | | |
|---|---|---|
| CA | 908529 A | 8/1972 |
| CA | 2451558 A1 | 1/2003 |

(Continued)

OTHER PUBLICATIONS

Extended European Search Report corresponding to International Application No. EP 14 18 4882.0 dated May 12, 2015.

(Continued)

*Primary Examiner* — Anna K Kinsaul
*Assistant Examiner* — Chinyere J Rushing-Tucker
(74) *Attorney, Agent, or Firm* — Carter, DeLuca & Farrell LLP

(57) ABSTRACT

An adapter assembly for connecting a loading unit to a handle assembly is provided. The adapter assembly includes a sleeve, a removable trocar assembly releasably securable with the sleeve, and a locking assembly configured to releasably secure the trocar assembly within the sleeve. The locking assembly includes first and second button members and corresponding first and second locking members for releasably securing the trocar assembly.

21 Claims, 11 Drawing Sheets

(56) References Cited

U.S. PATENT DOCUMENTS

| | | |
|---|---|---|
| 3,759,336 A | 9/1973 | Marcovitz et al. |
| 3,771,526 A | 11/1973 | Rudie |
| 4,162,399 A | 7/1979 | Hudson |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,717,063 A | 1/1988 | Ebihara |
| 4,722,685 A | 2/1988 | de Estrada et al. |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,823,807 A | 4/1989 | Russell et al. |
| 4,873,977 A | 10/1989 | Avant et al. |
| 4,874,181 A | 10/1989 | Hsu |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,129,118 A | 7/1992 | Walmesley |
| 5,129,570 A | 7/1992 | Schulze et al. |
| 5,139,513 A | 8/1992 | Segato |
| 5,152,744 A | 10/1992 | Krause et al. |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,301,061 A | 4/1994 | Nakada et al. |
| 5,309,927 A | 5/1994 | Welch |
| 5,312,023 A | 5/1994 | Green et al. |
| 5,312,024 A | 5/1994 | Grant et al. |
| 5,314,435 A | 5/1994 | Green et al. |
| 5,314,436 A | 5/1994 | Wilk |
| 5,326,013 A | 7/1994 | Green et al. |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,350,355 A | 9/1994 | Sklar |
| 5,355,897 A | 10/1994 | Pietrafitta et al. |
| 5,360,154 A | 11/1994 | Green |
| 5,368,215 A | 11/1994 | Green et al. |
| 5,383,874 A | 1/1995 | Jackson et al. |
| 5,383,880 A | 1/1995 | Hooven |
| 5,389,098 A | 2/1995 | Tsuruta et al. |
| 5,392,979 A | 2/1995 | Green et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,413,267 A | 5/1995 | Solyntjes et al. |
| 5,425,738 A | 6/1995 | Gustafson et al. |
| 5,427,087 A | 6/1995 | Ito et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,467,911 A | 11/1995 | Tsuruta et al. |
| 5,470,006 A | 11/1995 | Rodak |
| 5,474,223 A | 12/1995 | Viola et al. |
| 5,476,379 A | 12/1995 | Disel |
| 5,487,499 A | 1/1996 | Sorrentino et al. |
| 5,497,934 A | 3/1996 | Brady et al. |
| 5,503,635 A | 4/1996 | Sauer et al. |
| 5,518,163 A | 5/1996 | Hooven |
| 5,518,164 A | 5/1996 | Hooven |
| 5,522,534 A | 6/1996 | Viola et al. |
| 5,526,822 A | 6/1996 | Burbank et al. |
| 5,529,235 A | 6/1996 | Boiarski et al. |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,562,239 A | 10/1996 | Boiarski et al. |
| 5,588,579 A | 12/1996 | Schnut et al. |
| 5,609,285 A | 3/1997 | Grant et al. |
| 5,626,587 A | 5/1997 | Bishop et al. |
| 5,626,591 A | 5/1997 | Kockerling et al. |
| 5,632,432 A | 5/1997 | Schulze et al. |
| 5,632,433 A | 5/1997 | Grant et al. |
| 5,639,008 A | 6/1997 | Gallagher et al. |
| 5,641,111 A | 6/1997 | Ahrens et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,669,918 A | 9/1997 | Balazs et al. |
| 5,685,474 A | 11/1997 | Seeber |
| 5,693,042 A | 12/1997 | Boiarski et al. |
| 5,704,534 A | 1/1998 | Huitema et al. |
| 5,709,335 A | 1/1998 | Heck |
| 5,713,505 A | 2/1998 | Huiterna |
| 5,715,987 A | 2/1998 | Kelley et al. |
| 5,718,360 A | 2/1998 | Green et al. |
| 5,720,755 A | 2/1998 | Dakov |

(56) References Cited

U.S. PATENT DOCUMENTS

| | | |
|---|---|---|
| 5,732,872 A | 3/1998 | Bolduc et al. |
| 5,749,896 A | 5/1998 | Cook |
| 5,758,814 A | 6/1998 | Gallagher et al. |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,799,857 A | 9/1998 | Robertson et al. |
| 5,814,055 A | 9/1998 | Knodel et al. |
| 5,820,009 A | 10/1998 | Melling et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,863,159 A | 1/1999 | Lasko |
| 5,868,760 A | 2/1999 | McGuckin, Jr. |
| 5,881,943 A | 3/1999 | Heck et al. |
| 5,908,427 A | 6/1999 | McKean et al. |
| 5,915,616 A | 6/1999 | Viola et al. |
| 5,947,363 A | 9/1999 | Bolduc et al. |
| 5,951,576 A | 9/1999 | Wakabayashi |
| 5,954,259 A | 9/1999 | Viola et al. |
| 5,957,363 A | 9/1999 | Heck |
| 5,964,774 A | 10/1999 | McKean et al. |
| 5,993,454 A | 11/1999 | Longo |
| 5,993,468 A | 11/1999 | Rygaard |
| 6,010,054 A | 1/2000 | Johnson et al. |
| 6,017,354 A | 1/2000 | Culp et al. |
| 6,024,748 A | 2/2000 | Manzo et al. |
| 6,032,849 A | 3/2000 | Mastri et al. |
| 6,045,560 A | 4/2000 | McKean et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,090,123 A | 7/2000 | Culp et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,126,651 A | 10/2000 | Mayer |
| 6,129,547 A | 10/2000 | Cise et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,239,732 B1 | 5/2001 | Cusey |
| 6,241,139 B1 | 6/2001 | Milliman et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,264,087 B1 | 7/2001 | Whitman |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,338,737 B1 | 1/2002 | Toledano |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,434,507 B1 | 8/2002 | Clayton et al. |
| 6,439,446 B1 | 8/2002 | Perry et al. |
| 6,443,973 B1 | 9/2002 | Whitman |
| 6,450,390 B2 | 9/2002 | Heck et al. |
| 6,461,372 B1 | 10/2002 | Jensen et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,537,280 B2 | 3/2003 | Dinger et al. |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,610,066 B2 | 8/2003 | Dinger et al. |
| 6,611,793 B1 | 8/2003 | Burnside et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,645,218 B1 | 11/2003 | Cassidy et al. |
| 6,652,542 B2 | 11/2003 | Blatter et al. |
| 6,654,999 B2 | 12/2003 | Stoddard et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,699,177 B1 | 3/2004 | Wang et al. |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,820,791 B2 | 11/2004 | Adams |
| 6,821,282 B2 | 11/2004 | Perry et al. |
| 6,827,246 B2 | 12/2004 | Sullivan et al. |
| 6,830,174 B2 | 12/2004 | Hillstead et al. |
| 6,840,423 B2 | 1/2005 | Adams et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,852,122 B2 | 2/2005 | Rush |
| 6,860,892 B1 | 3/2005 | Tanaka et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,899,538 B2 | 5/2005 | Matoba |
| 6,905,057 B2 | 6/2005 | Swayze et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,922 B2 | 12/2005 | Bilotti et al. |
| 6,981,628 B2 | 1/2006 | Wales |

(56) References Cited

U.S. PATENT DOCUMENTS

| | | |
|---|---|---|
| 6,981,941 B2 | 1/2006 | Whitman et al. |
| 6,981,979 B2 | 1/2006 | Nicolo |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,331 B2 | 6/2006 | Adams et al. |
| 7,059,508 B2 | 6/2006 | Shelton, IV et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,111,769 B2 | 9/2006 | Wales et al. |
| 7,114,642 B2 | 10/2006 | Whitman |
| 7,118,528 B1 | 10/2006 | Piskun |
| 7,122,029 B2 | 10/2006 | Koop et al. |
| 7,122,044 B2 | 10/2006 | Bolduc et al. |
| 7,128,748 B2 | 10/2006 | Mooradian et al. |
| 7,140,528 B2 | 11/2006 | Shelton, IV |
| 7,141,049 B2 | 11/2006 | Stern et al. |
| 7,141,055 B2 | 11/2006 | Abrams et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,238,021 B1 | 7/2007 | Johnson |
| 7,246,734 B2 | 7/2007 | Shelton, IV |
| 7,252,660 B2 | 8/2007 | Kunz |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,328,828 B2 | 2/2008 | Ortiz et al. |
| 7,334,718 B2 | 2/2008 | McAlister et al. |
| 7,335,212 B2 | 2/2008 | Edoga et al. |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,137 B2 | 9/2008 | Manzo |
| 7,422,138 B2 | 9/2008 | Bilotti et al. |
| 7,422,139 B2 | 9/2008 | Shelton, IV et al. |
| 7,431,189 B2 | 10/2008 | Shelton, IV et al. |
| 7,431,191 B2 | 10/2008 | Milliman |
| 7,438,718 B2 | 10/2008 | Milliman et al. |
| 7,441,684 B2 | 10/2008 | Shelton, IV et al. |
| 7,448,525 B2 | 11/2008 | Shelton, IV et al. |
| 7,455,676 B2 | 11/2008 | Holsten et al. |
| 7,455,682 B2 | 11/2008 | Viola |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,556,186 B2 | 7/2009 | Milliman |
| 7,559,451 B2 | 7/2009 | Sharma et al. |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,585,306 B2 | 9/2009 | Abbott et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,600,663 B2 | 10/2009 | Green |
| 7,611,038 B2 | 11/2009 | Racenet et al. |
| 7,635,385 B2 | 12/2009 | Milliman et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,686,201 B2 | 3/2010 | Csiky |
| 7,694,864 B2 | 4/2010 | Okada et al. |
| 7,699,204 B2 | 4/2010 | Viola |
| 7,699,835 B2 | 4/2010 | Lee et al. |
| 7,708,181 B2 | 5/2010 | Cole et al. |
| 7,717,313 B2 | 5/2010 | Criscuolo et al. |
| 7,721,931 B2 | 5/2010 | Shelton, IV et al. |
| 7,721,932 B2 | 5/2010 | Cole et al. |
| 7,726,539 B2 | 6/2010 | Holsten et al. |
| 7,738,971 B2 | 6/2010 | Swayze et al. |
| 7,740,159 B2 | 6/2010 | Shelton, IV et al. |
| 7,743,958 B2 | 6/2010 | Orban, III |
| 7,743,960 B2 | 6/2010 | Whitman et al. |
| 7,744,627 B2 | 6/2010 | Orban, III et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,812 B2 | 9/2010 | Moore |
| 7,793,813 B2 | 9/2010 | Bettuchi |
| 7,799,039 B2 | 9/2010 | Shelton, IV et al. |
| 7,802,712 B2 | 9/2010 | Milliman et al. |
| 7,822,458 B2 | 10/2010 | Webster et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,534 B2 | 12/2010 | Viola et al. |
| 7,845,536 B2 | 12/2010 | Viola et al. |
| 7,845,537 B2 | 12/2010 | Shelton, IV et al. |
| 7,845,538 B2 | 12/2010 | Whitman |
| 7,857,185 B2 | 12/2010 | Swayze et al. |
| 7,857,187 B2 | 12/2010 | Milliman |
| 7,870,989 B2 | 1/2011 | Viola et al. |
| 7,886,951 B2 | 2/2011 | Hessler |
| 7,896,215 B2 | 3/2011 | Adams et al. |
| 7,900,805 B2 | 3/2011 | Shelton, IV et al. |
| 7,900,806 B2 | 3/2011 | Chen et al. |
| 7,905,897 B2 | 3/2011 | Whitman et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,230 B2 | 4/2011 | Whitman et al. |

(56) References Cited

U.S. PATENT DOCUMENTS

| | | |
|---|---|---|
| 7,918,377 B2 | 4/2011 | Measamer et al. |
| 7,922,061 B2 | 4/2011 | Shelton, IV et al. |
| 7,922,062 B2 | 4/2011 | Cole et al. |
| 7,922,719 B2 | 4/2011 | Ralph et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,947,034 B2 | 5/2011 | Whitman |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,959,050 B2 | 6/2011 | Smith et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,181 B2 | 6/2011 | Viola et al. |
| 7,975,895 B2 | 7/2011 | Milliman |
| 7,992,758 B2 | 8/2011 | Whitman et al. |
| 8,002,795 B2 | 8/2011 | Beetel |
| 8,006,701 B2 | 8/2011 | Bilotti et al. |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,020,741 B2 | 9/2011 | Cole et al. |
| 8,020,743 B2 | 9/2011 | Shelton, IV |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,052,024 B2 | 11/2011 | Viola et al. |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,114,118 B2 | 2/2012 | Knodel et al. |
| 8,123,103 B2 | 2/2012 | Milliman |
| 8,127,975 B2 | 3/2012 | Olson et al. |
| 8,128,645 B2 | 3/2012 | Sonnenschein et al. |
| 8,132,703 B2 | 3/2012 | Milliman et al. |
| 8,132,705 B2 | 3/2012 | Viola et al. |
| 8,136,712 B2 | 3/2012 | Zingman |
| 8,146,790 B2 | 4/2012 | Milliman |
| 8,146,791 B2 | 4/2012 | Bettuchi et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,181,838 B2 | 5/2012 | Milliman et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,220,367 B2 | 7/2012 | Hsu |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,235,273 B2 | 8/2012 | Olson et al. |
| 8,241,322 B2 | 8/2012 | Whitman et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,272,554 B2 | 9/2012 | Whitman et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,292,150 B2 | 10/2012 | Bryant |
| 8,292,888 B2 | 10/2012 | Whitman |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,342,379 B2 | 1/2013 | Whitman et al. |
| 8,343,185 B2 | 1/2013 | Milliman et al. |
| 8,348,130 B2 | 1/2013 | Shah et al. |
| 8,348,855 B2 | 1/2013 | Hillely et al. |
| 8,353,438 B2 | 1/2013 | Baxter, III et al. |
| 8,353,439 B2 | 1/2013 | Baxter, III et al. |
| 8,353,440 B2 | 1/2013 | Whitman et al. |
| 8,353,930 B2 | 1/2013 | Heinrich et al. |
| 8,357,144 B2 | 1/2013 | Whitman et al. |
| 8,360,295 B2 | 1/2013 | Milliman et al. |
| 8,365,633 B2 | 2/2013 | Simaan et al. |
| 8,365,972 B2 | 2/2013 | Aranyi et al. |
| 8,365,974 B2 | 2/2013 | Milliman |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,904 B2 | 4/2013 | Wenchell et al. |
| 8,418,905 B2 | 4/2013 | Milliman |
| 8,418,909 B2 | 4/2013 | Kostrzewski |
| 8,424,535 B2 | 4/2013 | Hessler et al. |
| 8,424,739 B2 | 4/2013 | Racenet et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,454,585 B2 | 6/2013 | Whitman |
| 8,485,414 B2 | 7/2013 | Criscuolo et al. |
| 8,490,853 B2 | 7/2013 | Criscuolo et al. |
| 8,505,802 B2 | 8/2013 | Viola et al. |
| 8,511,533 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,551,138 B2 | 10/2013 | Orban, III et al. |
| 8,561,871 B2 | 10/2013 | Rajappa et al. |
| 8,561,874 B2 | 10/2013 | Scirica |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,602,287 B2 | 12/2013 | Yates et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,623,000 B2 | 1/2014 | Humayun et al. |
| 8,627,995 B2 | 1/2014 | Smith et al. |
| 8,631,993 B2 | 1/2014 | Kostrzewski |
| 8,632,463 B2 | 1/2014 | Drinan et al. |
| 8,636,187 B2 | 1/2014 | Hueil et al. |
| 8,636,766 B2 | 1/2014 | Milliman et al. |
| 8,640,940 B2 | 2/2014 | Ohdaira |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,662,370 B2 | 3/2014 | Takei |

(56) References Cited

U.S. PATENT DOCUMENTS

| | | |
|---|---|---|
| 8,663,258 B2 | 3/2014 | Bettuchi et al. |
| 8,672,206 B2 | 3/2014 | Aranyi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,733,611 B2 | 5/2014 | Milliman |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,888,762 B2 | 11/2014 | Whitman |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,950,646 B2 | 2/2015 | Viola |
| 8,960,519 B2 | 2/2015 | Whitman et al. |
| 8,967,443 B2 | 3/2015 | McCuen |
| 8,968,276 B2 | 3/2015 | Zemlok et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 10,524,797 B2 | 1/2020 | Sgroi |
| 2001/0031975 A1 | 10/2001 | Whitman et al. |
| 2003/0038938 A1 | 2/2003 | Jung et al. |
| 2003/0111507 A1 | 6/2003 | Nunez |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0051597 A1 | 3/2005 | Toledano |
| 2005/0107813 A1 | 5/2005 | Gilete Garcia |
| 2005/0125027 A1 | 6/2005 | Knodel et al. |
| 2005/0131442 A1 | 6/2005 | Yachia et al. |
| 2006/0000869 A1 | 1/2006 | Fontayne |
| 2006/0011698 A1 | 1/2006 | Okada et al. |
| 2006/0085033 A1 | 4/2006 | Criscuolo et al. |
| 2006/0142656 A1 | 6/2006 | Malackowski et al. |
| 2006/0142744 A1 | 6/2006 | Boutoussov |
| 2006/0201989 A1 | 9/2006 | Ojeda |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023477 A1 | 2/2007 | Whitman et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0254094 A1 | 10/2009 | Knapp et al. |
| 2009/0299141 A1 | 12/2009 | Downey et al. |
| 2010/0019016 A1 | 1/2010 | Edoga et al. |
| 2010/0023022 A1 | 1/2010 | Zeiner et al. |
| 2010/0051668 A1 | 3/2010 | Milliman et al. |
| 2010/0069942 A1 | 3/2010 | Shelton, IV |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0225073 A1 | 9/2010 | Porter et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0077673 A1 | 3/2011 | Grubac et al. |
| 2011/0114697 A1 | 5/2011 | Baxter, III et al. |
| 2011/0114700 A1 | 5/2011 | Baxter, III et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0144640 A1 | 6/2011 | Heinrich et al. |
| 2011/0147432 A1 | 6/2011 | Heinrich et al. |
| 2011/0155783 A1 | 6/2011 | Rajappa et al. |
| 2011/0174099 A1 | 7/2011 | Ross et al. |
| 2011/0184245 A1 | 7/2011 | Xia et al. |
| 2011/0192882 A1 | 8/2011 | Hess et al. |
| 2011/0204119 A1 | 8/2011 | McCuen |
| 2011/0218522 A1 | 9/2011 | Whitman |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0061448 A1 | 3/2012 | Zingman |
| 2012/0089131 A1 | 4/2012 | Zemlok et al. |
| 2012/0111921 A1 | 5/2012 | Wenchell |
| 2012/0143002 A1 | 6/2012 | Aranyi et al. |
| 2012/0145755 A1 | 6/2012 | Kahn |
| 2012/0172924 A1 | 7/2012 | Allen, IV |
| 2012/0193395 A1 | 8/2012 | Pastorelli et al. |
| 2012/0193398 A1 | 8/2012 | Williams et al. |
| 2012/0211542 A1 | 8/2012 | Racenet |
| 2012/0223121 A1 | 9/2012 | Viola et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0310220 A1 | 12/2012 | Malkowski et al. |
| 2012/0310228 A1 | 12/2012 | Bonn et al. |
| 2012/0323226 A1 | 12/2012 | Chowaniec et al. |
| 2012/0325888 A1 | 12/2012 | Qiao et al. |
| 2013/0015232 A1 | 1/2013 | Smith et al. |
| 2013/0018361 A1 | 1/2013 | Bryant |
| 2013/0020372 A1 | 1/2013 | Jankowski et al. |
| 2013/0020373 A1 | 1/2013 | Smith et al. |
| 2013/0032628 A1 | 2/2013 | Li et al. |

(56) References Cited

U.S. PATENT DOCUMENTS

| | | |
|---|---|---|
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214025 A1 | 8/2013 | Zemlok et al. |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0274722 A1 | 10/2013 | Kostrzewski et al. |
| 2013/0277411 A1 | 10/2013 | Hodgkinson et al. |
| 2013/0277412 A1 | 10/2013 | Gresham et al. |
| 2013/0282052 A1 | 10/2013 | Aranyi |
| 2013/0284792 A1 | 10/2013 | Ma |
| 2013/0292449 A1 | 11/2013 | Bettuchi et al. |
| 2013/0292451 A1 | 11/2013 | Viola et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0008413 A1 | 1/2014 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0012317 A1 | 1/2014 | Orban et al. |
| 2014/0025046 A1 | 1/2014 | Williams et al. |
| 2014/0110455 A1 | 4/2014 | Ingmanson et al. |
| 2014/0166728 A1* | 6/2014 | Swayze ............ A61B 17/1155 227/179.1 |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0133957 A1 | 5/2015 | Kostrzewski |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |

FOREIGN PATENT DOCUMENTS

| | | |
|---|---|---|
| CA | 2824590 A1 | 4/2014 |
| CN | 102247182 A | 11/2011 |
| DE | 1057729 B | 5/1959 |
| DE | 3301713 A1 | 7/1984 |
| DE | 102008053842 A1 | 5/2010 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0705571 A1 | 4/1996 |
| EP | 1354560 A2 | 10/2003 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2524656 A2 | 11/2012 |
| EP | 2524658 A1 | 11/2012 |
| EP | 3078335 A1 | 10/2016 |
| ES | 2333509 A1 | 2/2010 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 08038488 | 2/1996 |
| JP | 2005125075 A | 5/2005 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 0154594 A1 | 8/2001 |
| WO | 2008107918 A1 | 9/2008 |
| WO | 2011108840 A2 | 9/2011 |
| WO | 2012/040984 A1 | 4/2012 |

OTHER PUBLICATIONS

Canadian Office Action corresponding to International Application No. CA 2640399 dated May 7, 2015.

Japanese Office Action corresponding to International Application No. JP 2011-197365 dated Mar. 23, 2015.

Japanese Office Action corresponding to International Application No. JP 2011-084092 dated May 20, 2015.

Japanese Office Action corresponding to International Application No. JP 2014-148482 dated Jun. 2, 2015.

Extended European Search Report corresponding to International Application No. EP 14 18 9358.6 dated Jul. 8, 2015.

Extended European Search Report corresponding to International Application No. EP 14 19 6148.2 dated Apr. 23, 2015.

Partial European Search Report corresponding to International Application No. EP 14 19 6704.2 dated May 11, 2015.

Australian Office Action corresponding to International Application No. AU 2010241367 dated Aug. 20, 2015.

Partial European Search Report corresponding to International Application No. EP 14 19 9783.3 dated Sep. 3, 2015.

Extended European Search Report corresponding to International Application No. EP 15 16 9962.6 dated Sep. 14, 2015.

European Search Report dated May 23, 2017, issued in EP Application No. 17151213.

(56) References Cited

OTHER PUBLICATIONS

Australian Office Action dated Nov. 27, 2020, issued in corresponding AU Appln. No. 2016277583, 4 pages.

* cited by examiner

ADAPTER ASSEMBLY INCLUDING A REMOVABLE TROCAR ASSEMBLY

CROSS-REFERENCE TO RELATED APPLICATIONS

This application is a continuation of U.S. patent application Ser. No. 14/994,457, filed Jan. 13, 2016, now U.S. Pat. No. 10,524,797, the disclosure of which is incorporated by reference herein in its entirety.

BACKGROUND

Technical Field

The present disclosure relates to reusable surgical stapling devices. More particularly, the present disclosure relates to reusable adapter assemblies including a removable trocar assembly for use with a circular stapler.

Background of Related Art

Surgical devices for applying staples, clips, or other fasteners to tissue are well known. Typically, endoscopic stapling devices include an actuation unit, i.e., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly. The adapter assembly may include an extension.

The adapter assembly may be reusable. To facilitate sterilization and cleaning of the adapter assembly, it would be beneficial to have an adapter assembly including a removable trocar assembly.

SUMMARY

An adapter assembly for connecting a loading unit to a handle assembly is provided. The adapter assembly includes a sleeve, a trocar assembly releasably securable with the sleeve, and a locking assembly configured to releasably secure the trocar assembly within the sleeve. The locking assembly includes first and second button members, and corresponding first and second locking members selectively movable in response to movement of the first and second button members. The first and second locking members are configured for selective reception within the respective first and second locking openings of the trocar housing.

In embodiments, the first and second locking members are moveable between a first position where the trocar assembly is securely received within the sleeve and a second position where the trocar assembly is removable from within the sleeve. The first and second button members may be configured to move the respective first and second locking members between the first position and the second position. The first and second locking members may be biased to the first position by respective first and second springs. The first and second locking members may maintain the respective first and second button members in an outward position when the first and second locking members are in the first position.

The locking assembly of the adapter assembly may further include an internal housing defining first and second recesses. The first and second button members may be received within the respective first and second recesses. The internal housing may further define first and second apertures. The first and second locking members may be received within the respective first and second apertures. The internal housing may also define at least one flush port. The adapter assembly may further include inner and outer flexible band assemblies. In addition, the adapter assembly may include a base, and a handle rotatably secured to the base, wherein a proximal end of the sleeve is fixedly secured to the handle to permit rotation of the sleeve.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
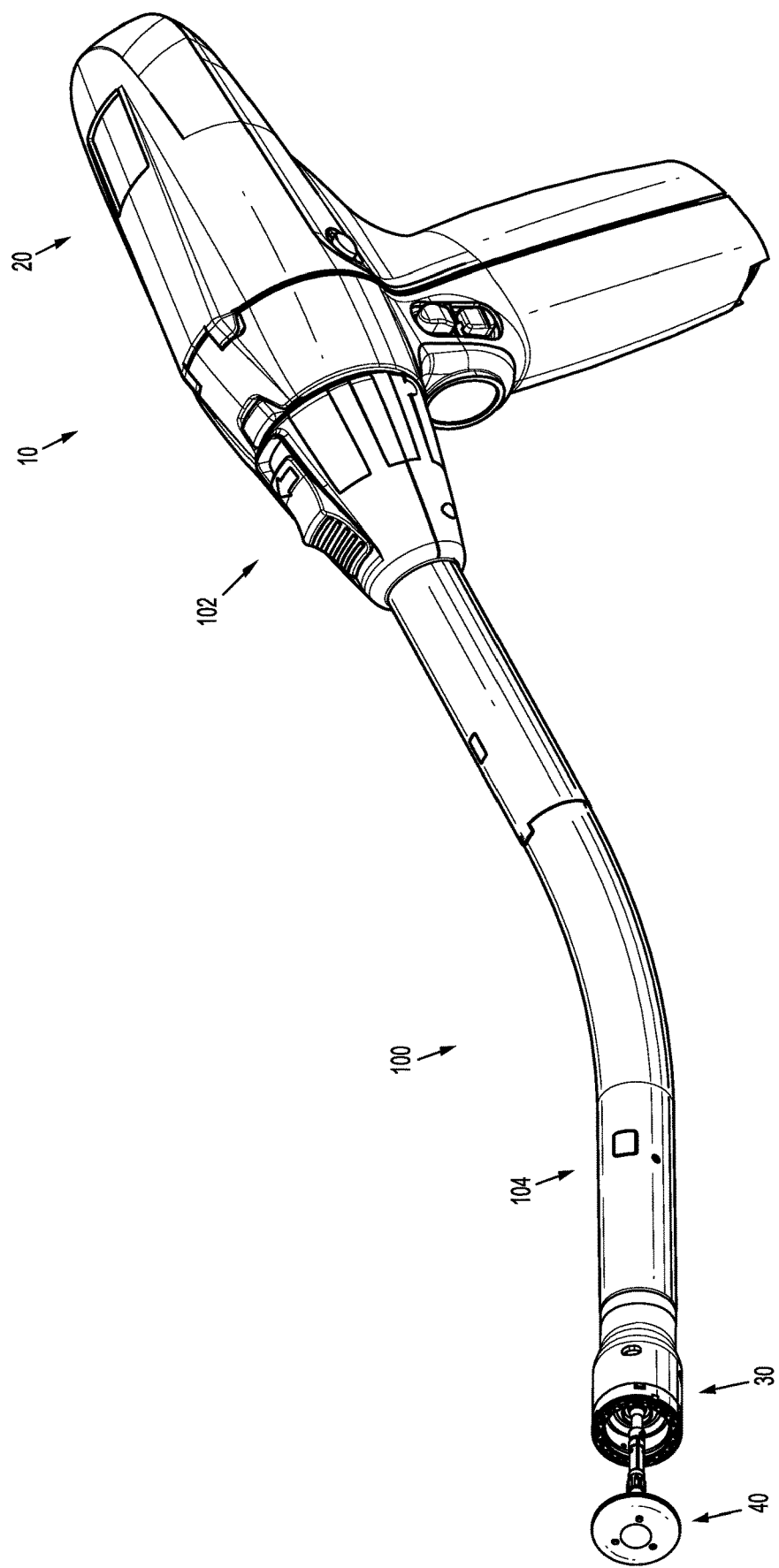
FIG. 1 is a perspective view of a surgical stapling device including an handle assembly with an adapter assembly according to an embodiment of the present disclosure.

Embodiments of the presently disclosed reusable adapter assembly including a removable trocar assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring initially to FIG. 1, an adapter assembly according to an embodiment of the present disclosure, shown generally as adapter assembly 100, is a component of a surgical stapling device 10. The surgical stapling device 10 further includes a powered handle assembly 20, a loading unit 30, and an anvil assembly 40. Although shown and described with reference to surgical stapling device 10, the aspects of the present disclosure may be modified for use with manual surgical stapling devices having various configurations, and with powered surgical stapling devices having alternative configurations. For a detailed description of exemplary surgical stapling devices, please refer to commonly owned U.S. Pat. No. 9,023,014 ("the '014 patent) and U.S. Pat. Appl. Publ. No. 2012/0253329 ("the '329 publication"), the contents of each of which are incorporated by reference herein in their entirety.

The adapter assembly 100 includes a proximal portion 102 configured for operable connection to the handle assembly 20 and a distal portion 104 configured for operable connection to the loading unit 30 and to the anvil assembly 40. Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the present disclosure. For a detailed description of an exemplary adapter assembly, please refer to commonly owned U.S. patent application Ser. No. 14/875,766 ("the '766 application"), the contents of which is incorporated by reference herein in its entirety.

Figure 2:
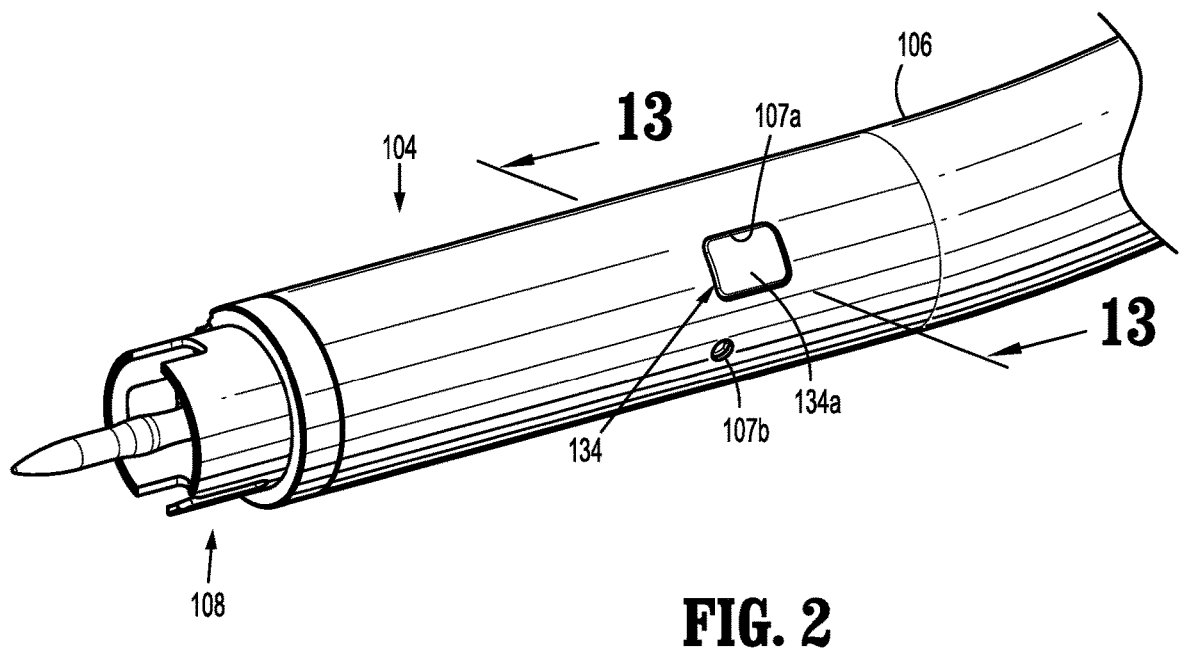
FIG. 2 is a perspective view of a distal end of the adapter assembly shown in FIG. 1.
Figure 3:
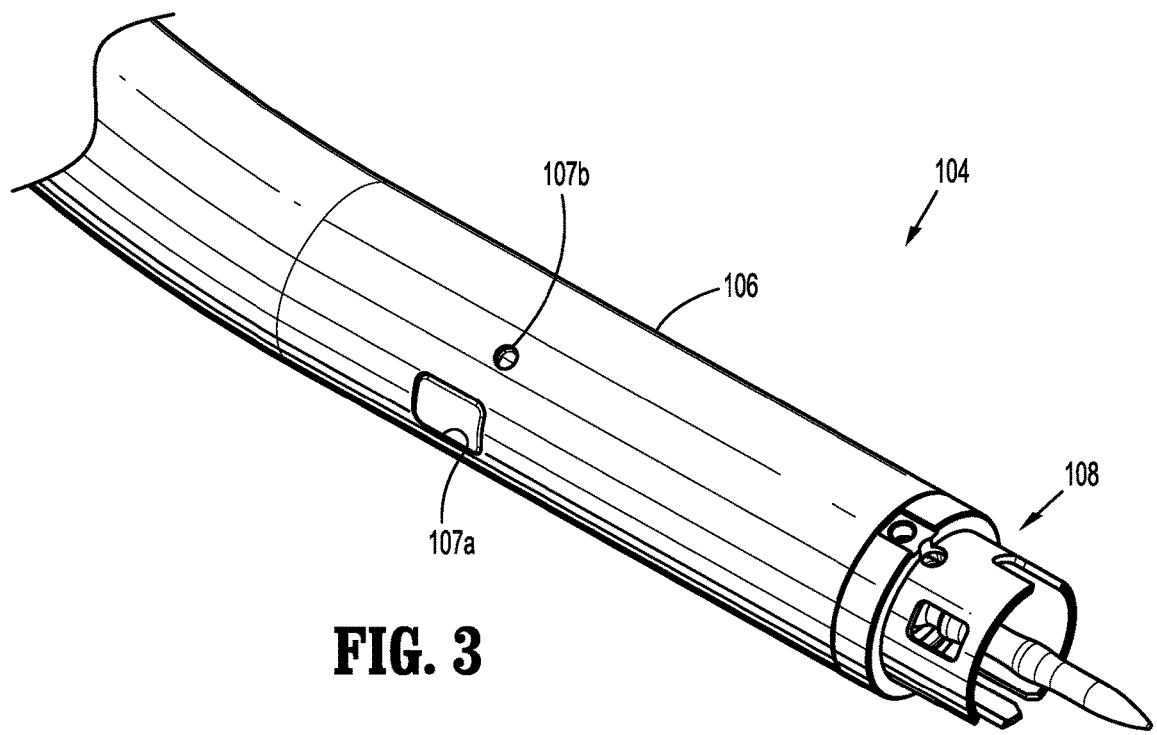
FIG. 3 is another perspective view of the distal end of the adapter assembly shown in FIG. 1.

With additional reference to FIGS. 2 and 3, the adapter assembly 100 includes an outer sleeve 106, and a connector housing 108 secured to a distal end of the outer sleeve 106. The connector housing 108 is configured to releasably secure an end effector, e.g., the loading unit 30 (FIG. 1), to the adapter assembly 100.

Figure 4:
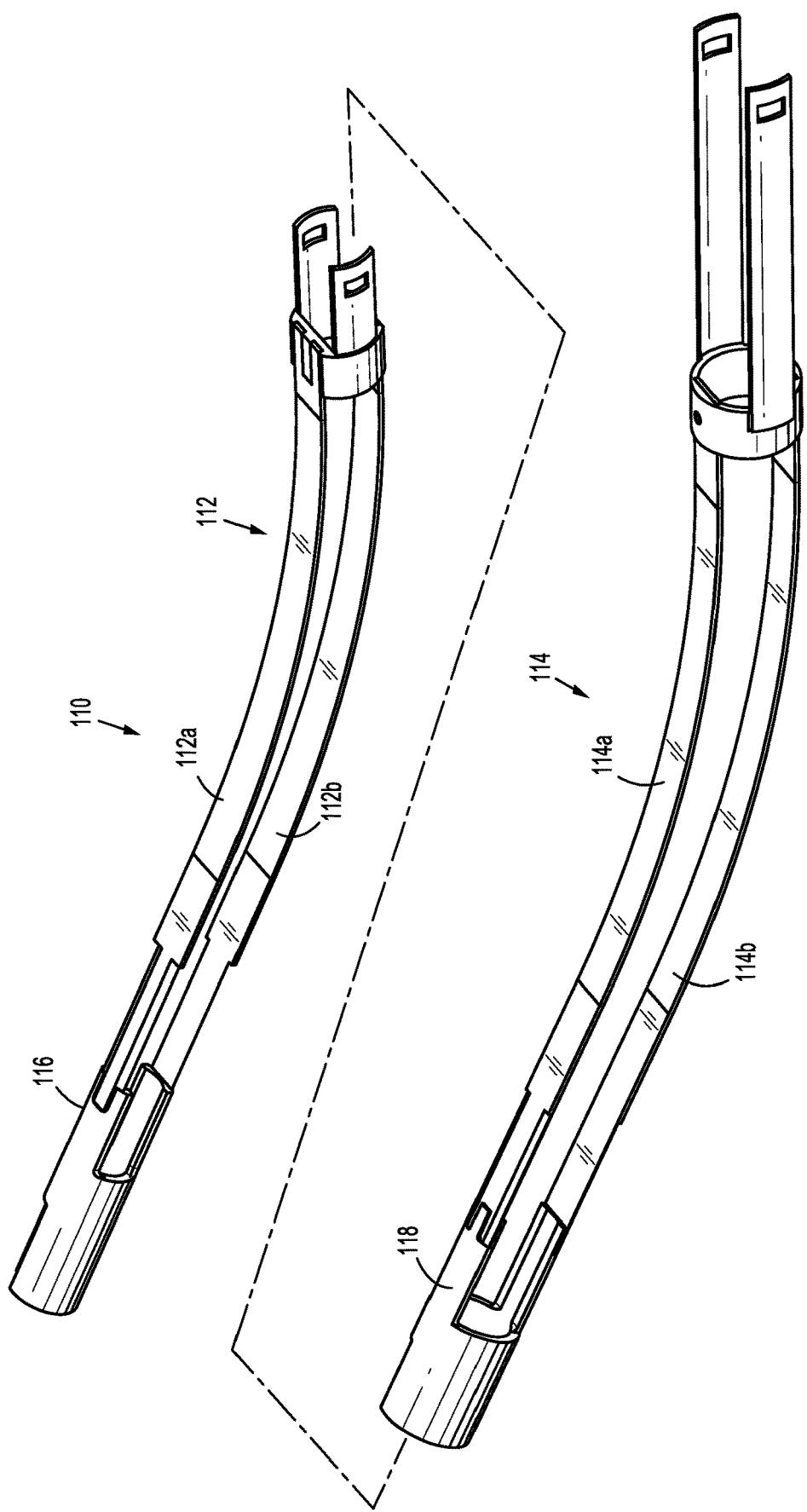
FIG. 4 is a perspective view of a drive assembly of the adapter assembly shown in FIG. 1, with components separated.

Turning briefly to FIG. 4, the adapter assembly 100 (FIG. 2) includes a drive assembly 110 extending through the outer sleeve 106 (FIG. 13) of the adapter assembly 100, and includes an inner flexible band assembly 112 and an outer flexible band assembly 114. The inner flexible band assembly 112 includes first and second flexible bands 112a, 112b, and an inner pusher member 116 connected to the distal ends of the first and second flexible bands 112a, 112b. Similarly, the outer flexible band assembly 114 includes first and second flexible bands 114a, 114b, and an outer pusher member 118. For a detailed description of the structure and function of the drive assembly 110, please refer to the '766 application, the content of which was previously incorporated herein by reference in its entirety.

Figure 5:
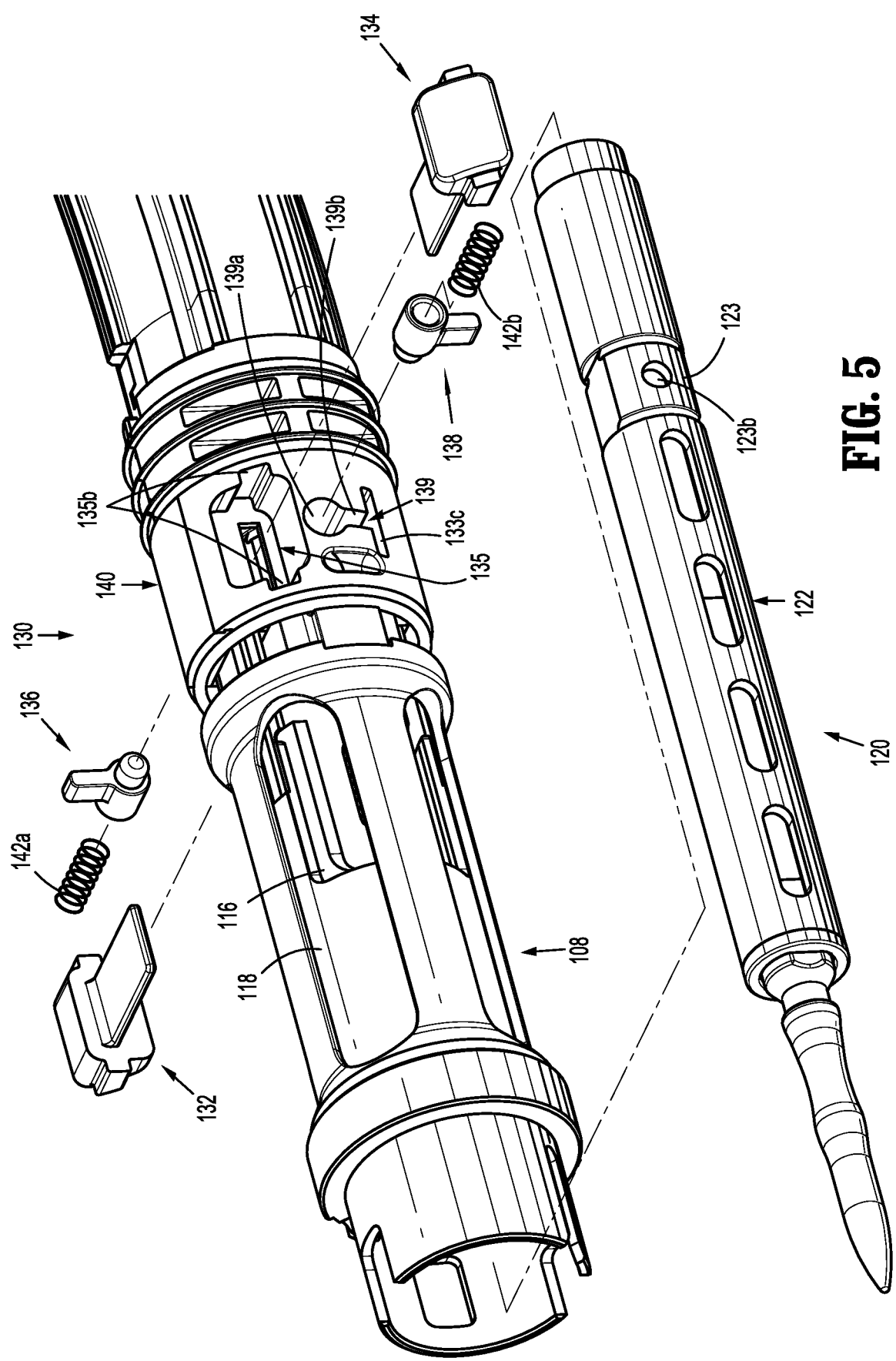
FIG. 5 is a side perspective view of a distal end of the adapter assembly shown in FIG. 1 with the sleeve removed, a locking assembly with parts separated, and a removable trocar assembly removed.

With reference now to FIG. 5, the adapter assembly 100 further includes a trocar assembly 120 configured to attach to, and selectively position an anvil assembly, i.e., anvil assembly 40 (FIG. 1), relative to the loading unit 30 (FIG. 1), and a locking assembly 130 that releasably secures the trocar assembly 120 relative to the outer sleeve 106 of the adapter assembly 100. The trocar assembly 120 will only be described to the extent necessary to fully disclose the aspects of the present disclosure. For a detailed description of the structure and function of an exemplary trocar assembly, please refer to the '766 application, the content of which was previously incorporated by reference herein in its entirety.

Figure 6:
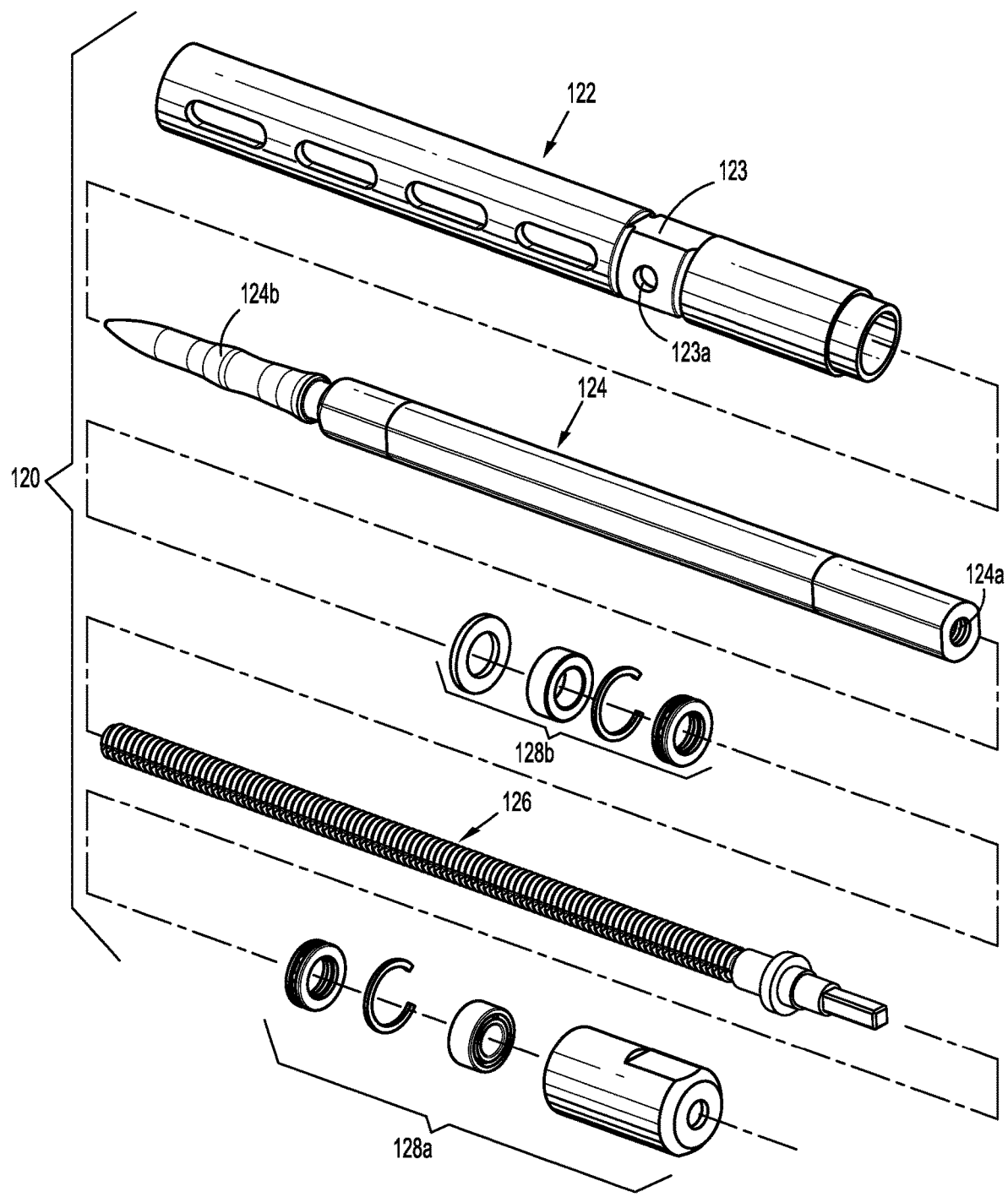
FIG. 6 is a perspective view of the removable trocar assembly shown in FIG. 5, with parts separated.

Briefly, and with additional reference to FIG. 6, the trocar assembly 120 of the adapter assembly 100 (FIG. 1) includes an outer housing 122, a trocar member 124 slidably disposed within the outer housing 122, and a drive screw 126 operably received within the trocar member 124 for axially moving the trocar member 124 relative to the outer housing 122. More specifically, the trocar member 124 defines a threaded bore 124a which is dimensioned to receive the drive screw 126. The outer surface of the drive screw 126 is threaded such that rotation of the drive screw 126 causes longitudinal movement of the trocar member 124 within the outer housing 122 of the trocar assembly 120. A distal end 124b of trocar member 124 is configured to releasably engage an anvil assembly, e.g., the anvil assembly 40 (FIG. 1). Proximal and distal bearing assemblies 128a, 128a are mounted to a proximal end of outer housing 122 of trocar assembly 120 for rotatably supporting the drive screw 126 within the outer housing 122 and the trocar member 124. As will be described in further detail below, the outer housing 122 includes a cutout 123 defining first and second locking openings 123a, 123b (FIG. 15) for receiving the respective locking portions 136c, 138c of the respective first and second locking members 136, 138 (FIG. 11) of the locking assembly 130 of the adapter assembly 100.

Referring back to FIG. 5, the locking assembly 130 of the adapter assembly 100 (FIG. 2) includes an internal housing 140 disposed within the outer sleeve 106 (FIG. 2) of the adapter assembly 100, first and second button members 132, 134 movably supported within the internal housing 140, and first and second locking members 136, 138 in operable engagement with the respective first and second button members 132, 134. As will be described in further detail below, each of the first and second button members 132, 134 and the first and second locking members 136, 138 are movably supported within the internal housing 140. Movement of the first and second button members 132, 134 is configured to move the respective first and second locking members 136, 138 from a locked position (FIG. 13) to an unlocked position (FIG. 15) against the bias of first and second springs 142a, 142b, respectively, engaged by the first and second locking members 136, 138, respectively.

Figure 7:
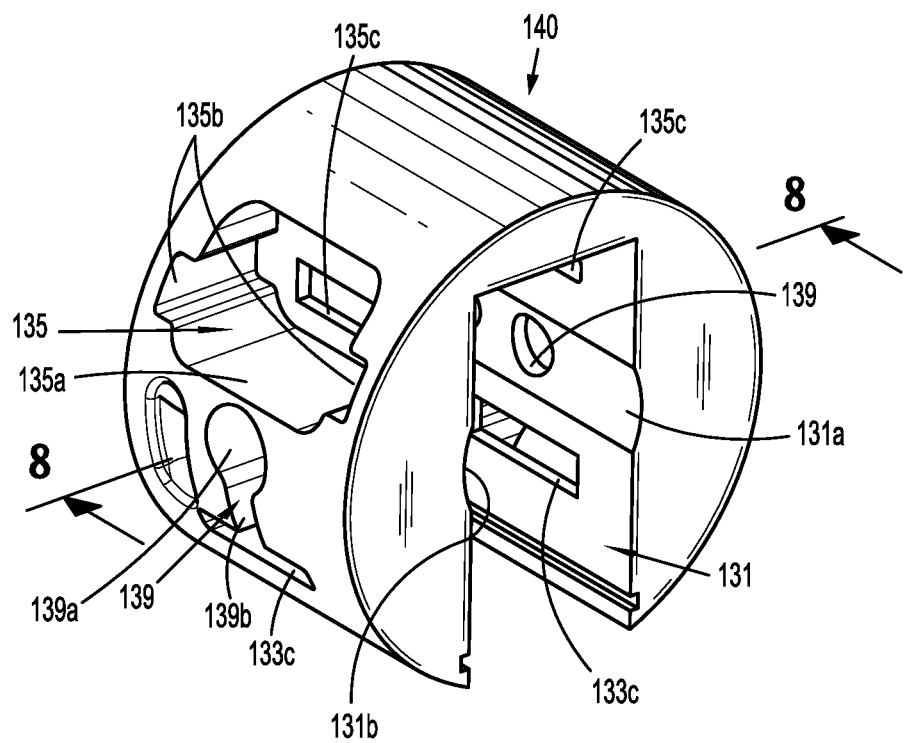
FIG. 7 is a side perspective view of an internal housing of the locking assembly of the adapter assembly shown in FIG. 1.
Figure 8:
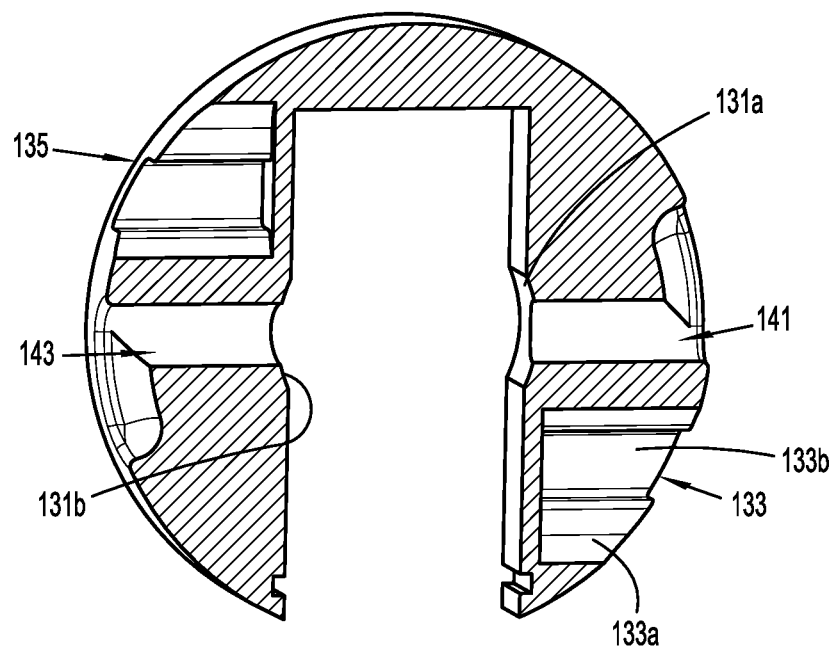
FIG. 8 is a cross-sectional end view taken along section line 8-8 shown in FIG. 7.

With additional reference to FIGS. 7 and 8, the internal housing 140 of the locking assembly 130 includes a substantially cylindrical body defining a rectangular cutout 131 extending a length thereof through which the drive assembly 110 (FIG. 4) and trocar assembly 120 (FIG. 6) are received. In particular, the internal housing 140 defines longitudinal grooves 131a, 131b extending along either side of the cutout 131 for receiving the outer housing 122 (FIG. 5) of the trocar assembly 120 (FIG. 5).

Figure 9:
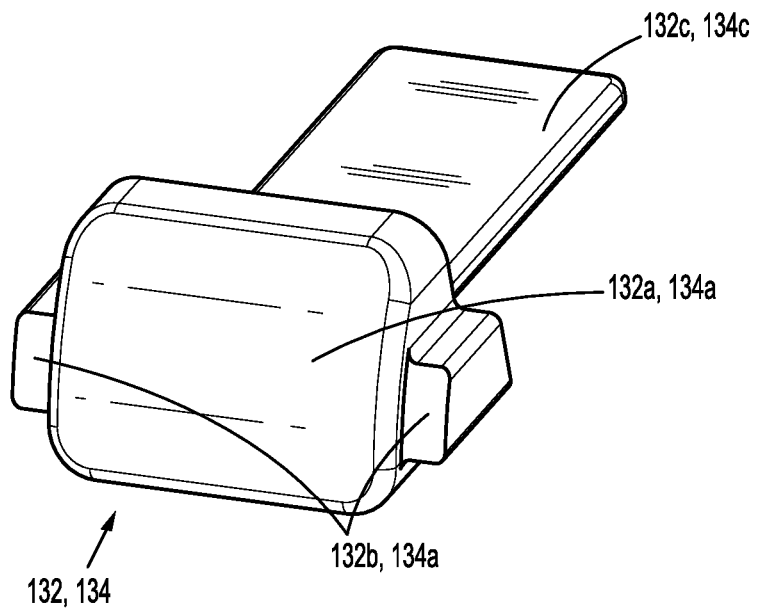
FIG. 9 is a side perspective view of a button member of the locking assembly shown in FIG. 5.

The internal housing 140 further defines first and second recesses 133, 135 in fluid communication with the cutout 131. Each of the first and second recesses 133, 135 is configured to operably receive the respective first and second button members 132, 134 (FIG. 9). More particularly, the first and second recesses 133, 135 include an enlarged portion 133a, 135a, respectively, for accommodating a base portion 132a, 134a (FIG. 9) of the respective first and second button members 132, 134. The first and second recess 133, 134 further include first and second slots 133b, 135b extending across the rectangular cutout 131 for accommodating a stem portion 132b, 134b (FIG. 9) of the respective first and second button members 132, 134. Each of the enlarged portions 133a, 135a of the first and second recesses 133a, 135a includes a pair of grooves 133c, 135c for slidingly receiving tab portions 132c, 134c (FIG. 9) extending from each of the base portions 132a, 134a, respectively, of the respective first and second button members 132, 134.

With continued reference to FIGS. 7 and 8, the internal housing 140 further defines first and second apertures 137, 139 (FIG. 13) in fluid communication with the cutout 131. The first and second apertures 137, 139 are configured to operably receive the respective first and second locking members 136, 138. More particularly, each of the first and second apertures 137, 139 includes a cylindrical portion 137a, 139a (FIG. 13), respectively, for accommodating a base portion 136a, 138a of the respective first and second locking members 136, 138, a rectangular portion 137b, 139b (FIG. 13) for accommodating a flange portion 136b, 138b of the respective first and second locking members 136, 138, and openings 137c, 139c (FIG. 13) extending into the rectangular cutout 131 for receiving locking portions 136c, 138c, respectively, of the respective first and second locking member 136, 138. As will be described in further detail below, the first recess 133 aligns with the second aperture 139, and the second recess 135 aligns with the first aperture 137 such that the first button member 132 engages the second locking member 138 and the second button member 134 engages the first locking member 136.

The internal housing 140 of the locking assembly 130 also defines first and second flush ports 141, 143 in fluid communication with the cutout 131. The first and second flush ports 141, 143 facilitate cleaning of the adapter assembly 100 following removal of the trocar assembly 120. The outer sleeve 106 of the adapter assembly 100 defines a pair of openings 107b (FIGS. 2 and 3) corresponding to the flush ports 141, 143. An insert 144 is receivable within the cutout 131 of the internal housing 140 of the locking assembly 130 for maintaining alignment of the drive assembly 110 through the internal housing 140.

Turning briefly to FIG. 9, as noted above, each of the first and second button members 132, 134 includes the base portion 132a, 134a, tab portions 132c, 134c, respectively, and the stem portion 132b, 134b, respectively, extending from the respective base portion 132a, 134a.

Figure 10:
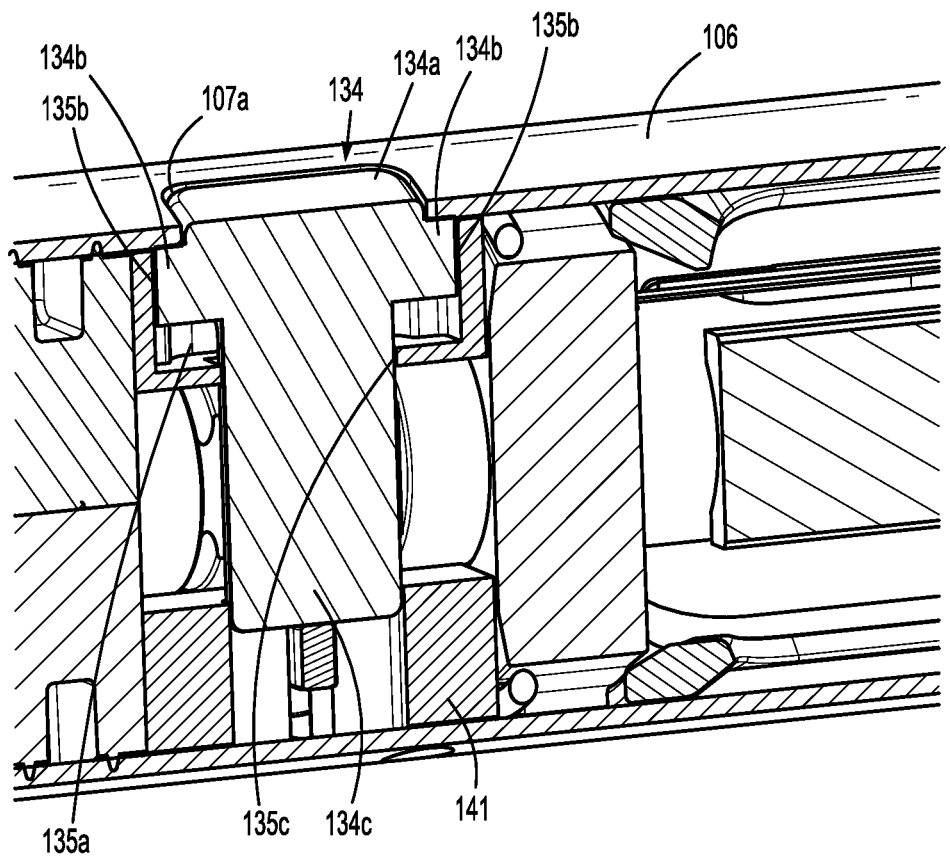
FIG. 10 is a cross-sectional top view taken along section line 10-10 shown in FIG. 13.

With particular reference to FIG. 10, the second button member 134 is received within the second recess 135 of the internal housing 140 with the base portion 134a received within the enlarged portion 135a of the second recess 135, the tab portion 134b is received within the respective grooves 135b of the second recess 135, and the stem portion 134c is received within the slot 135c of the second recess 135. The opening 107a in the outer sleeve 106, through which the second button member 134 protrudes, is dimensioned such that the tab portions 134b engage the outer sleeve 106 and retain the second button member 134 within the second recess 135. Although only the second button member 134 is shown and described in detail, the first button member 132 is similarly situated within the first recess 133.

Figure 11:
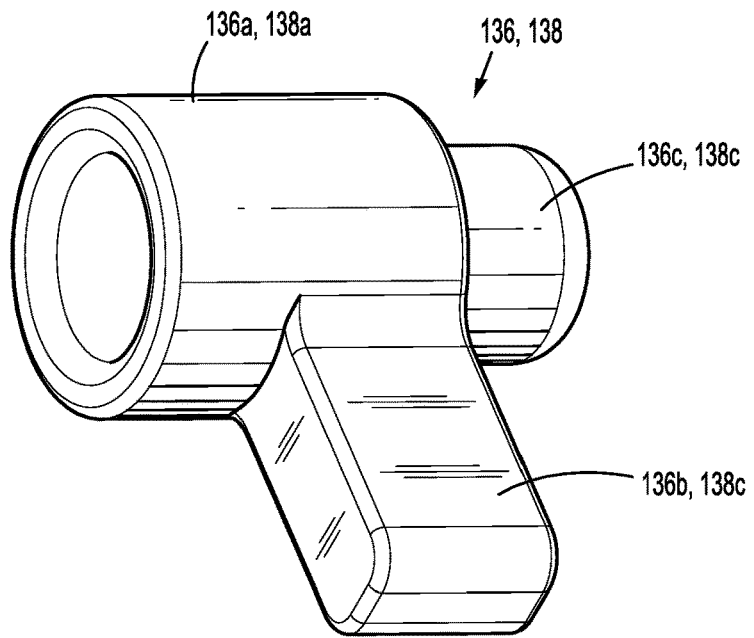
FIG. 11 is side perspective view of a locking member of the locking assembly shown in FIG. 5.

With reference now to FIG. 11, the first and second locking members 136, 138 each include the base portions 136a, 138a, respectively, the flange portions 136b, 138b extending outwardly from the respective base portions 136a, 138a, and the locking portions 136c, 138c extending from the respective base portions 136a, 138a. As shown, the base portions 136a, 138a and the locking portions 136c, 138c are substantially cylindrical. It is envisioned that either or both of the base portions 136a, 138a and the locking portions 136c, 138c may be any suitable shape. As will be described in further detail below, the first and second locking members 136, 138 operate to releasably secure the trocar assembly 120 within the outer sleeve 106 of the adapter assembly 100.

Figure 12:
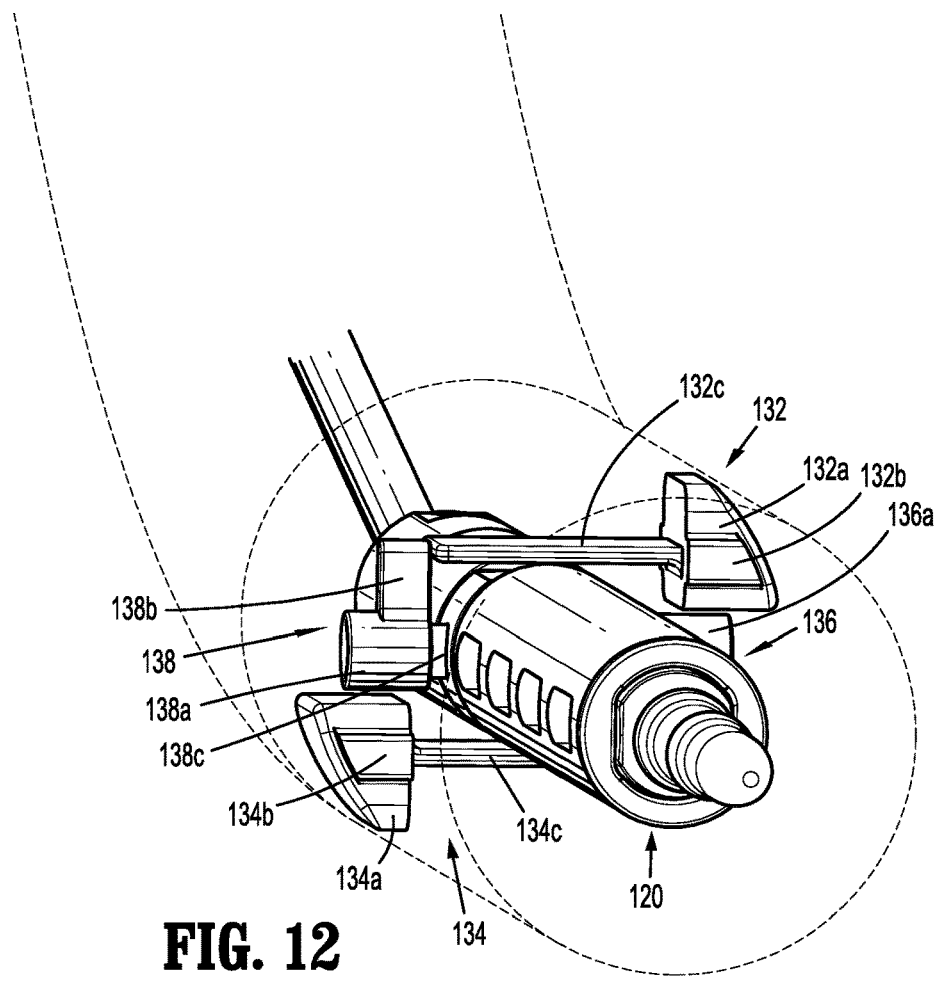
FIG. 12 is a perspective end view of the trocar assembly and locking assembly shown in FIG. 5, with the outer sleeve shown in phantom and the internal housing removed.
Figure 13:
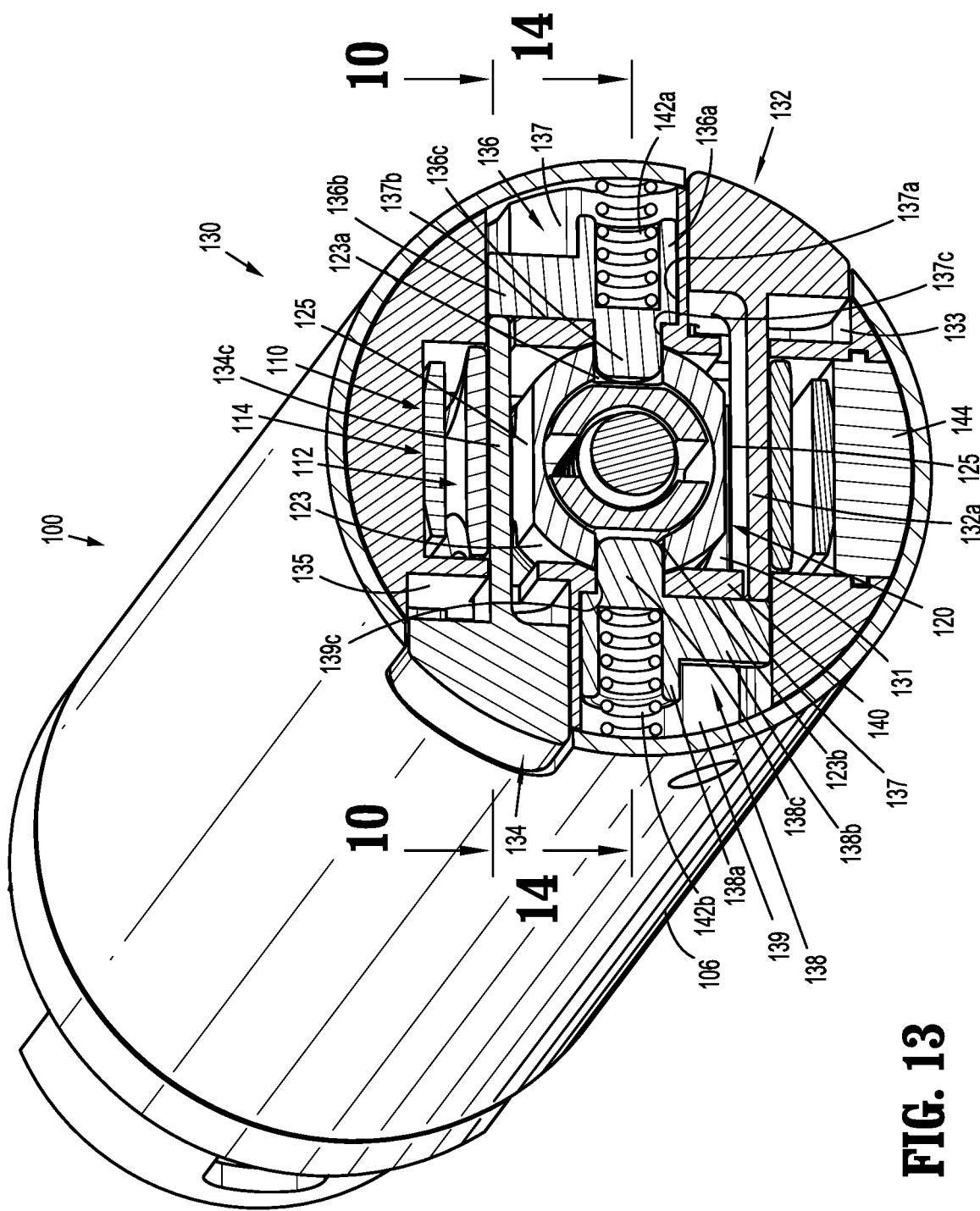
FIG. 13 a cross-sectional end view taken along section line 13-13 shown in FIG. 2.
Figure 14:
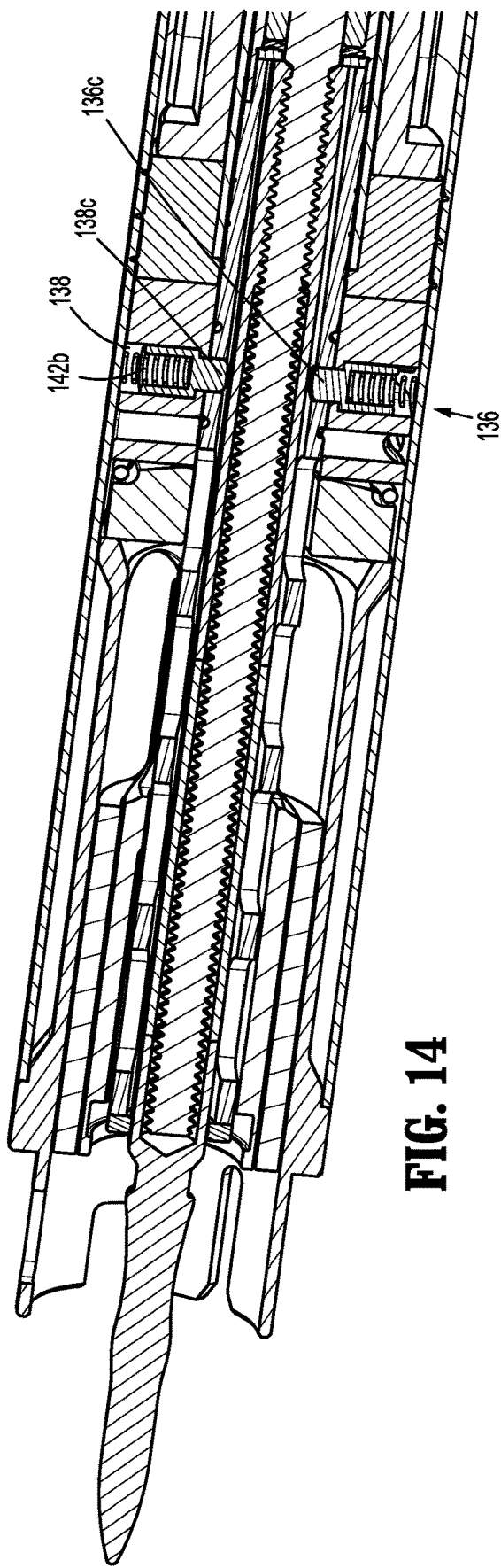
FIG. 14 is a cross-sectional side view taken along section line 14-14 shown in FIG. 13.

The operation of the locking assembly 130 of the adapter assembly 100 will now be described with reference to FIGS. 12-17. Referring initially to FIGS. 12-14, the locking assembly 130 is shown in the locked configuration, i.e., with the first and second locking members 136, 138 in their first position. More particularly, the first and second locking members 136, 138 of the locking assembly 130 are biased by the respective first and second springs 142a, 142b such that the locking portions 136c, 138c of the respective first and second locking members 136, 138 are received within the first and second locking openings 123a, 123b, respectively, formed in the outer housing 122 of the trocar assembly 120.

In the locked configuration, the stem portions 132b, 134b of the respective first and second button members 132, 134 of the locking assembly 130 extend across the cutout 131 of the internal housing 140 and engage the respective flange portions 136b, 138b of the first and second locking members 136, 138, respectively. The first and second button members 132, 134 are maintained in an initial position through engagement of the second and first locking members 138, 136, respectively, and the inward bias of the respective first and second spring 142b, 142a.

Figure 14A:
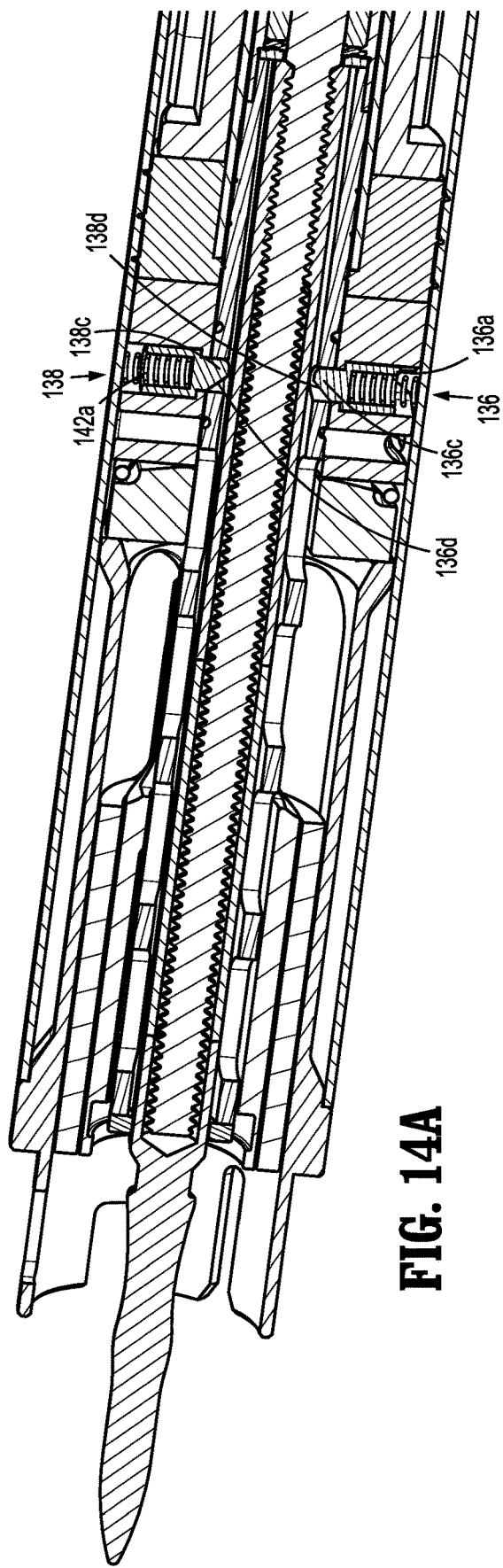
FIG. 14A is a cross-sectional side view of an adapter assembly according to an alternative embodiment of the present disclosure, taken along section 14-14 shown in FIG. 13.

The trocar assembly 120 of adapter assembly 100 may be provided preloaded within outer sleeve 106 of the adapter assembly 100, or the trocar assembly 120 may be provided separated from the adapter assembly 100. If provided as a separate component, the trocar assembly 120 is loaded through a distal end of the outer sleeve 106 of the adapter assembly 100 prior to attaching an end effector, e.g., the end effector 30, to the connector housing 108 of the adapter assembly 100. The trocar assembly 120 is fed into the outer sleeve 106 of the adapter assembly 100 through the cutout 131 of the internal housing 140. In order to receive the trocar assembly 120 through the internal housing 140, the locking assembly 130 is moved to the unlocked position (FIG. 16), in a manner as will be described in detail below. Alternatively, and with reference to FIG. 14A, the first and second locking members 136, 138 may include a chamfered distal surface 136d, 138d that, when engaged by a proximal end of the trocar assembly 120, pushes the first and second locking members 136, 138 against the bias of the first and second spring 142a, 142b to the unlocked position to permit passage of the trocar assembly 120 through the cutout 131 of the internal housing 140.

Upon alignment of the first and second locking openings 123a, 123b of the outer housing 122 of the trocar assembly 120 with the locking portions 136c, 138c of the respective first and second locking members 136, 138, the first and second springs 142a, 142b bias the locking portions 136c, 138c of the first and second locking members 136, 138 into the respective first and second locking openings 123a, 123b of the outer housing 122. An audible and/or tactile indication may be provided to a user by the locking assembly 130 as the first and second locking members 136, 138 are received with the respective first and second locking openings 123a, 123b to indicate that the trocar assembly 120 is securely received within the locking assembly 130.

In embodiments, the outer housing 122 of the trocar assembly 120 includes flat portions 125 (FIG. 13) for maintaining rotational alignment of the trocar assembly 120 relative to the locking assembly 130 to ensure that the first and second locking openings 123a, 123b of the trocar assembly 120 are maintained in alignment with the respective first and second locking members 136, 138 of the locking assembly 130.

Once the trocar assembly 120 is loaded within the sleeve 106, and secured therein by the locking assembly 130, the adapter assembly 100, the attached handle assembly 20 (FIG. 1), the attached loading unit 30 (FIG. 1), and the attached anvil assembly 40 (FIG. 1) operate in a traditional manner.

Following a surgical stapling procedure using the surgical stapling device 10, the trocar assembly 120 of the adapter assembly 100 is removed from the sleeve 106 of the adapter assembly 100 to facilitate cleaning and/or sterilizing of the adapter assembly 100. As noted above, the simultaneous pressing of the first and second button members 132, 134 of the locking mechanism 130 disengages the first and second locking members 136, 138 from the trocar assembly 120. The distal end 124b of the trocar member 124 may be grasped and pulled relative to outer sleeve 108 to remove the trocar assembly 120 from the adapter assembly 100. By requiring both the first and second button members 132, 134 to be depressed simultaneously to unlock the lock assembly 130, accidental release of the trocar assembly 120 is prevented in the event of inadvertent pressing of only one of the first and second button members 132, 134.

Figure 15:
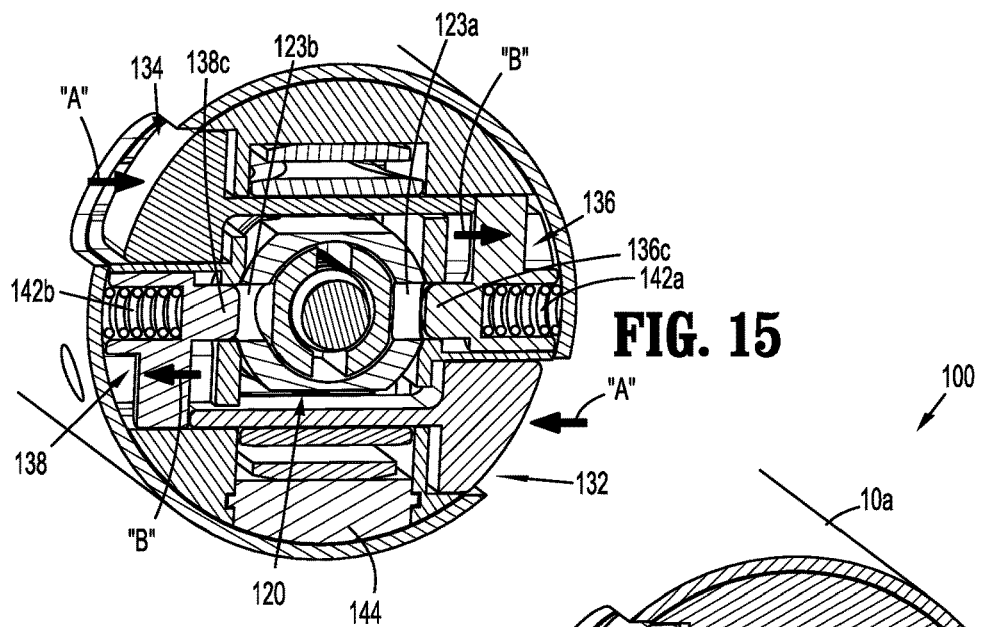
FIG. 15 is a cross-sectional perspective end view of taken along section lines 13-13 shown in FIG. 2 with the locking assembly in an unlocked condition.
Figure 16:
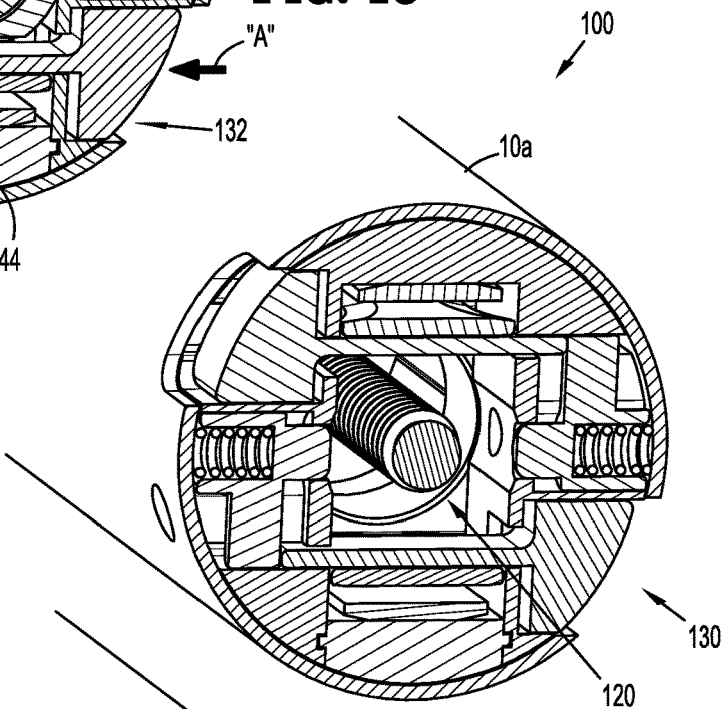
FIG. 16 is a cross-sectional perspective end view of taken along section lines 13-13 shown in FIG. 2 with the locking assembly in an unlocked condition and the trocar assembly being retracted.
Figure 17:
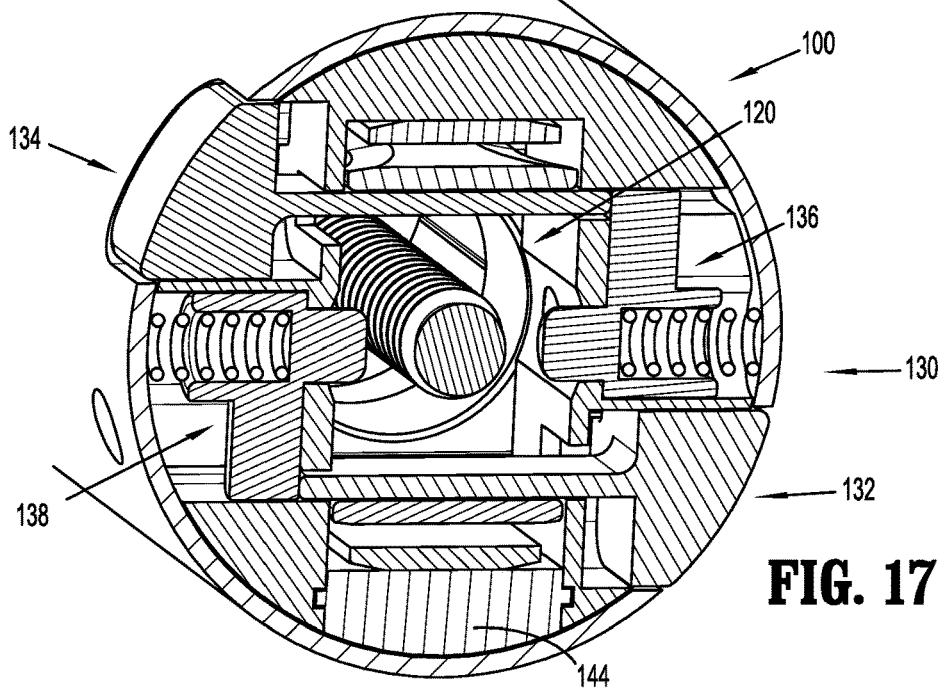
FIG. 17 is an enlarged view of the cross-sectional perspective end view shown in FIG. 16.

With reference to FIGS. 15-17, the locking assembly 130 of the adapter assembly 100 is shown with the first and second locking members 136, 138 in their second or unlocked position. To move the first and second locking members 136, 138 to the unlocked position, the second and first button members 134, 132, respectively, are depressed, as indicated by arrows "A" in FIG. 15. Engagement of the stem portions 138c, 136c of the respective second and first button members 134, 132 with the flange portions 136b, 138b, respectively, of the respective first and second locking members 136, 138 moves the first and second locking members 136, 138 against the bias of the first and second springs 142a, 142b radially outward, as indicated by arrows "B" in FIG. 15.

When the first and second locking members 136, 138 are in the second position, the locking portions 136c, 138c of the respective first and second locking members 136, 138 are withdrawn from the respective first and second locking openings 123a, 123b of the outer housing 122 of the trocar assembly 120, and the trocar assembly 120 is removable from within the outer sleeve 106 of the adapter assembly 100. Once the trocar assembly 120 is separated from the adapter assembly 100, the adapter assembly 100 may be cleaned and/or sterilized in a traditional manner.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A locking mechanism for releasably securing a trocar assembly within a sleeve of an adapter assembly, the locking mechanism comprising:
    a housing supportable within the sleeve of the adapter assembly;
    first and second button members supported within the housing and selectively movable between a first position and a second position;
    first and second locking members corresponding to the first and second button members, the first and second locking members being selectively movable in response to movement of the respective first and second button members, the first and second locking members being configured for selective reception within respective first and second locking openings of the trocar assembly; and,
    first and second springs configured to bias the respective first and second locking members to a locked position.

2. The locking mechanism of claim 1, wherein the first and second locking members move from the locked position to an unlocked position in response to the respective first and second button members moving from the first position to the second position.

3. The locking mechanism of claim 2, wherein the first and second locking members are configured to be received within the respective first and second locking openings in the trocar assembly when the first and second locking members are in the locked position.

4. The locking mechanism of claim 3, wherein the first and second locking members are configured to be laterally spaced from the respective first and second locking openings in the trocar assembly when the first and second locking members are in the unlocked position.

5. The locking mechanism of claim 1, wherein the housing defines first and second recesses, the first and second button members being received within the respective first and second recesses.

6. The locking mechanism of claim 5, wherein the housing defines first and second apertures, the first and second locking members being received within the respective first and second apertures.

7. The locking mechanism of claim 6, wherein the housing further defines at least one flush port.

8. The locking mechanism of claim 1, wherein the first and second locking members move in parallel relation to one another.

9. The locking mechanism of claim 1, wherein the first and second button members move in parallel relation to one another.

10. An adapter assembly configured to connect a loading unit to a handle assembly, the adapter assembly comprising:
    a sleeve;
    a trocar assembly releasably securable within the sleeve, the trocar assembly including a trocar housing defining first and second locking openings; and
    a locking mechanism for releasably securing the trocar assembly within the sleeve, the locking mechanism including:
    a housing supported within the sleeve;
    first and second button members supported within the housing and selectively movable between a first position and a second position;
    first and second locking members corresponding to the first and second button members, the first and second locking members being selectively movable in response to movement of the respective first and second button members, the first and second locking members being configured for selective reception within the respective first and second locking openings of the trocar assembly; and, first and second springs configured to bias the respective first and second locking members to a locked position.

11. The adapter assembly of claim 10, wherein the first and second locking members move from the locked position to an unlocked position in response to the respective first and second button members moving from the first position to the second position.

12. The adapter assembly of claim 11, wherein the first and second locking members are configured to be received within the respective first and second locking openings in the trocar assembly when the first and second locking members are in the locked position.

13. The adapter assembly of claim 12, wherein the first and second locking members are configured to be laterally spaced from the respective first and second locking openings in the trocar assembly when the first and second locking members are in the unlocked position.

14. The adapter assembly of claim 10, wherein the housing defines first and second recesses, the first and second button members being received within the respective first and second recesses.

15. The adapter assembly of claim 14, wherein the housing defines first and second apertures, the first and second locking members being received within the respective first and second apertures.

16. The adapter assembly of claim 15, wherein the housing further defines at least one flush port.

17. The adapter assembly of claim 10, wherein the first and second locking members move in parallel relation to one another.

18. The adapter assembly of claim 10, wherein the first and second button members move in parallel relation to one another.

19. The adapter assembly of claim 10, further including inner and outer flexible band assemblies.

20. The adapter assembly of claim 10, further including a base, and a handle rotatably secured to the base, wherein a proximal end of the sleeve is fixedly secured to the handle to permit rotation of the sleeve.

21. A locking mechanism for releasably securing a trocar assembly within a sleeve of an adapter assembly, the locking mechanism comprising:

a housing supportable within the sleeve of the adapter assembly;

first and second button members supported within the housing and selectively movable between a first position and a second position;

first and second locking members corresponding to the first and second button members, the first and second locking members being selectively movable in response to movement of the respective first and second button members between a locked position and an unlocked position, the unlocked position being radially spaced outward of the locked position, the first and second locking members being configured for selective reception within respective first and second locking openings of the trocar assembly; and, first and second biasing members configured to bias the respective first and second locking members to a locked position.

* * * * *